(12) United States Patent
Todd et al.

(10) Patent No.: US 6,361,941 B1
(45) Date of Patent: Mar. 26, 2002

(54) CATALYTIC NUCLEIC ACID-BASED DIAGNOSTIC METHODS

(75) Inventors: Alison V. Todd, Glebe; Caroline J. Fuery, Sydney; Murray J. Cairns, Woy Woy, all of (AU)

(73) Assignee: Johnson & Johnson Research Pty Limited, Eyeleigh (AU)

( * ) Notice: Subject to any disclaimer, the term of this patent is extended or adjusted under 35 U.S.C. 154(b) by 0 days.

(21) Appl. No.: 09/270,140

(22) Filed: Mar. 16, 1999

Related U.S. Application Data

(60) Provisional application No. 60/079,651, filed on Mar. 27, 1998.

(51) Int. Cl.[7] ............................. C12Q 1/68; C12P 19/34
(52) U.S. Cl. .......................................... 435/6; 435/91.5
(58) Field of Search ..................................... 435/6, 91.5

(56) References Cited

U.S. PATENT DOCUMENTS 5,807,718 A * 9/1998 Joyce et al. ................ 435/91.5

OTHER PUBLICATIONS

Kashani–Sabet M. et al., "Reversal of the Malignant Phenotype by an Anti–ras Ribozyme", Antisense Research and Development, vol. 2, pp. 3–15 (1992).*

* cited by examiner

*Primary Examiner*—Kenneth R. Horlick
*Assistant Examiner*—Teresa Strzelecka
(74) *Attorney, Agent, or Firm*—Myra McCormack

(57) ABSTRACT

This invention provides methods and kits useful for determining whether a subject is afflicted with a disorder characterized by the presence of one or more known nucleic acid mutations. The instant methods comprise steps of nucleic acid molecule isolation, amplification, contact with one or more catalytic nucleic acid molecules specifically cleaving a target sequence present either in the case of disorder or wild-type, but not both, and determining cleavage of the amplified segment(s).

16 Claims, No Drawings

CATALYTIC NUCLEIC ACID-BASED DIAGNOSTIC METHODS

This application claims priority from U.S. Provisional Patent Application No. 60/079,651 filed Mar. 27, 1998 and entitled "Catalytic Nucleic Acid-based Diagnostic Methods."

Throughout this application, various publications are cited. The disclosure of these publications is hereby incorporated by reference into this application to describe more fully the state of the art to which this invention pertains.

FIELD OF THE INVENTION

This invention relates to methods of diagnosing disorders characterized by known nucleic acid mutations. The instant methods employ the use of catalytic nucleic acid molecules, and are useful in connection with diagnosing such disorders as cancer and AIDS.

BACKGROUND OF THE INVENTION

A variety of inherited and acquired diseases are associated with genetic variations such as point mutations, deletions and insertions. Some of these variations are directly associated with the presence of disease, while others correlate with disease risk and/or prognosis. There are more than 500 human genetic diseases which result from mutations in single genes (21, 22). These include cystic fibrosis, muscular dystrophy, α1-antitrypsin deficiency, phenylketonuria, sickle cell anemia or trait, and various other hemoglobinopathies (21, 22). Furthermore, individuals with increased susceptibility to several common polygenic conditions, such as atherosclerotic heart disease, have been shown to have an association with the inheritance of particular DNA sequence polymorphisms.

Cancer is thought to develop due to the accumulation of genetic lesions in genes involved in cellular proliferation or differentiation. The ras proto-oncogenes, K-ras, N-ras and H-ras, and the p53 tumor suppressor gene are examples of genes which are frequently mutated in human cancers. Specific mutations in these genes leads to an increase in transforming potential. Genetic analysis would be invaluable in the clinic for assessing disease risk, diagnosis of disease, predicting a patient's prognosis or response to therapy, and monitoring a patient's progress. The introduction of such genetic tests, however, will depend on the development of simple, inexpensive, and rapid assays for genetic variations.

Methods of in vitro nucleic acid amplification have widespread applications in genetics and disease diagnosis. In the last decade many techniques for amplification of nucleic acid have been described. These include the polymerase chain reaction (PCR) (1–7), the ligase chain reaction (LCR) (8), the strand displacement amplification assay (SDA) (9) and transcription-mediated amplification (TMA) (10, 11) (also known as self-sustained sequence replication (SSR)). The amplification products (amplicons) produced by PCR, LCR and SDA are DNA, whereas RNA amplicons are produced by TMA. DNA or RNA templates, generated by these protocols or others, can be analyzed for the presence of sequence variation (i.e. mutation) associated with the disease to be ascertained.

As with nucleic acid amplification, catalytic nucleic acids have been studied intensively in recent years. The potential for suppression of gene function using catalytic nucleic acids as therapeutic agents is widely discussed in the literature (12–18). Catalytic RNA molecules (ribozymes) have been shown to be capable of cleaving both RNA (12) and DNA (17) molecules. Similarly, catalytic DNA molecules (DNAzymes) have also been shown to be capable of cleaving both RNA (13, 19) and DNA (18) molecules. Catalytic nucleic acid can only cleave a target nucleic acid sequence, provided that target sequence meets minimum sequence requirements. The target sequence must be complementary to the hybridizing regions of the catalytic nucleic acid and the target must contain a specific sequence at the site of cleavage. Examples of such sequence requirements at the cleavage site include the requirement for a purine:pyrmidine sequence for a class of DNAzyme cleavage (10–23 model) (19), and the requirement for the sequence uridine:H where H can equal A, C or U but not G, for the hammerhead ribozymes (23).

In addition to their therapeutic potential, catalytic nucleic acid molecules can also distinguish between targets which differ by a single point mutation (14–16). This is achieved by targeting a specific sequence which is present in wild-type but not mutant templates or vice versa. So far, this capacity for discrimination has only been exploited as a method for therapeutic manipulation of gene expression.

A review by Nollau-Wagener (24) compared several methodologies for the detection of point mutations with respect to the type of nucleic acid analyzed, the percentage of mutations detected, the time and cost of performing the assay, and problems relating to the use of toxic reagents. Each of the methodologies examined had its drawbacks. For example, denaturing gradient gel electrophoresis is time consuming, RNAase A cleavage can only detect about 70% of possible mutations, and chemical cleavage involves the use of toxic substances.

Another method, known as restriction fragment length polymorphism (RFLP), involves ascertaining whether a restriction enzyme site is present or absent at the locus of interest. In rare instances, mutations can be detected because they happen to lie within a naturally occurring restriction endonuclease recognition/cleavage site (31).

The inclusion of mismatched bases within primers used to facilitate in vitro amplification can result in the induction of artificial restriction endonuclease recognition/cleavage sites, and hence an increase in the number of loci which can be analyzed by RFLP (32). Modified primers containing mismatched bases have been used to induce artificial recognition/cleavage sites for restriction endonucleases at critical codons within the ras gene family (33–35). The general rules for designing primers which contain mismatched bases located near the 3' termini of primers have been established (36).

Although the use of mismatched primers has expanded the utility of RFLP analysis, the technique is still limited by the fact that a minimum of four base pairs is required for recognition and cleavage by a restriction enzyme.

SUMMARY OF THE INVENTION

This invention provides a method of determining whether a subject is afflicted with a disorder characterized by the presence of a known nucleic acid mutation, which comprises the steps of (a) isolating a sample of nucleic acid molecules from the subject; (b)(i) amplifying the nucleic acid segment present in the isolated sample, which segment is known to contain the mutation in a subject afflicted with the disorder, and (ii) under suitable conditions, contacting the resulting amplified segment with a catalytic nucleic acid molecule which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and (c) determining whether the catalytic nucleic acid molecule in step (b)(ii) cleaves the amplified segment, so as to determine whether the subject is afflicted with the disorder.

This invention also provides a method of determining whether a subject is afflicted with a disorder characterized by the presence of a plurality of known nucleic acid mutations, which comprises the steps of (a) isolating a sample of nucleic acid molecules from the subject; (b)(i) amplifying the nucleic acid segment present in the isolated sample, which segment is known to contain the plurality of mutations in a subject afflicted with the disorder, and (ii) under suitable conditions, contacting the resulting amplified segment with a plurality of catalytic nucleic acid molecules, each of which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and (c) determining whether each of the catalytic nucleic acid molecules in step (b)(ii) cleaves the amplified segment, so as to determine whether the subject is afflicted with the disorder.

This invention further provides a method of determining whether a subject is afflicted with a disorder characterized by the presence of a plurality of known nucleic acid mutations, which comprises the steps of (a) isolating a sample of nucleic acid molecules from the subject; (b) (i) amplifying the nucleic acid segments present in the isolated sample, which segments collectively are known to contain the plurality of mutations in a subject afflicted with the disorder, and (ii) under suitable conditions, contacting the resulting amplified segments with a plurality of catalytic nucleic acid molecules, each of which specifically recognizes and cleaves a target sequence present either (1) in one of the nucleic acid segments having one of the known mutations or (2) in the corresponding wild-type nucleic acid segment, but not both, with the proviso that step (ii) can be performed either subsequent to or concurrently with step (i); and (c) determining whether each of the catalytic nucleic acid molecules in step (b)(ii) cleaves the amplified segment containing its respective target sequence, so as to determine whether the subject is afflicted with the disorder.

Finally, this invention provides kits for use in practicing the instant diagnostic methods. The first instant kit comprises (a) a catalytic nucleic acid molecule which specifically recognizes and cleaves a target sequence present either (i) in a nucleic acid segment having a mutation known to be characteristic of a disorder or (ii) in the corresponding wild-type nucleic acid segment, but not both, and (b) a nucleic acid reagent suitable for use in amplifying the nucleic acid segment containing the target sequence.

The second instant kit comprises (a) a 10-23 DNAzyme which specifically recognizes and cleaves a target sequence present either (i) in a nucleic acid segment having a mutation known to be characteristic of a disorder or (ii) in the corresponding wild-type nucleic acid segment, but not both, and (b) a DNA primer suitable for initiating amplification of the segment under polymerase chain reaction conditions, which primer contains at least one purine ribonucleotide residue which serves as the 5' side of the site within the amplified segment recognized and cleaved by the 10-23 DNAzyme.

The third instant kit comprises (a) a first DNA primer which comprises a zymogene encoding a 10-23 DNAzyme that specifically recognizes and cleaves a target sequence present either (i) in a nucleic acid segment having a mutation known to be characteristic of a disorder or (ii) in the corresponding wild-type nucleic acid segment, but not both, which first primer is suitable for initiating amplification of the segment under polymerase chain reaction conditions; and (b) a second DNA primer suitable for initiating amplification of the segment under polymerase chain reaction conditions, which second primer contains at least one purine ribonucleotide residue which serves as the 5' side of the site within the amplified segment recognized and cleaved by the 10-23 DNAzyme, such that, upon amplification, (i) the resulting amplified nucleic acid molecule comprises the 10-23 DNAzyme, and (ii) the amplified nucleic acid segment is recognized and cleaved in cis by the DNAzyme.

DETAILED DESCRIPTION OF THE INVENTION

This invention provides methods employing catalytic nucleic acids to determine whether a subject is afflicted with a disorder characterized by the presence of one or more known nucleic acid mutations. These methods are collectively applicable to scenarios where the disorder is characterized by (i) a single mutation within a single nucleic acid segment, or (ii) a plurality of mutations within a single nucleic acid segment, or (iii) a plurality of mutations within a plurality of nucleic acid segments. For each mutation tested for by nucleic acid amplification, specific cleavage, and analysis, the instant methods provide a "yes or no" answer as to whether the mutation exists. This answer in turn ultimately leads to a "yes or no" answer as to whether the corresponding disorder is present in the subject.

Specifically, this invention provides a method of determining whether a subject is afflicted with a disorder characterized by the presence of a known nucleic acid mutation, which comprises the steps of (a) isolating a sample of nucleic acid molecules from the subject; (b)(i) amplifying the nucleic acid segment present in the isolated sample, which segment is known to contain the mutation in a subject afflicted with the disorder, and (ii) under suitable conditions, contacting the resulting amplified segment with a catalytic nucleic acid molecule which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and (c) determining whether the catalytic nucleic acid molecule in step (b)(ii) cleaves the amplified segment, so as to determine whether the subject is afflicted with the disorder.

This invention also provides a method of determining whether a subject is afflicted with a disorder characterized by the presence of a plurality of known nucleic acid mutations, which comprises the steps of (a) isolating a sample of nucleic acid molecules from the subject; (b)(i) amplifying the nucleic acid segment present in the isolated sample, which segment is known to contain the plurality of mutations in a subject afflicted with the disorder, and (ii) under suitable conditions, contacting the resulting amplified segment with a plurality of catalytic nucleic acid molecules, each of which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and (c) determining whether each of the catalytic nucleic acid molecules in step (b)(ii)

cleaves the amplified segment, so as to determine whether the subject is afflicted with the disorder.

This invention further provides a method of determining whether a subject is afflicted with a disorder characterized by the presence of a plurality of known nucleic acid mutations, which comprises the steps of (a) isolating a sample of nucleic acid molecules from the subject; (b) (i) amplifying the nucleic acid segments present in the isolated sample, which segments collectively are known to contain the plurality of mutations in a subject afflicted with the disorder, and (ii) under suitable conditions, contacting the resulting amplified segments with a plurality of catalytic nucleic acid molecules, each of which specifically recognizes and cleaves a target sequence present either (1) in one of the nucleic acid segments having one of the known mutations or (2) in the corresponding wild-type nucleic acid segment, but not both, with the proviso that step (ii) can be performed either subsequent to or concurrently with step (i); and (c) determining whether each of the catalytic nucleic acid molecules in step (b)(ii) cleaves the amplified segment containing its respective target sequence, so as to determine whether the subject is afflicted with the disorder.

The instant methods can be used to diagnose disorders in any subject. As used herein, "subject" means any animal, including, for example, mice, rats, dogs, guinea pigs, ferrets, rabbits, and primates. In the preferred embodiment, the subject is a human.

The disorder diagnosed by the instant invention can be any disorder characterized by the presence of at least one known nucleic acid mutation, which mutation is missing when such disorder is absent. Such disorders are well known in the art and include, by way of example, cancer, AIDS, cystic fibrosis, muscular dystrophy, α1-anti-trypsin deficiency, phenylketonuria, sickle cell anemia or trait, and various other hemoglobinopathies. In one embodiment, the disorder is selected from the group consisting of cancer, AIDS, and cystic fibrosis. In the preferred embodiment, the disorder is cancer. In the Experimental Details section which follows, numerous examples are given of specific mutations, target sequences containing same, and catalytic nucleic acids used for diagnosing such disorders as cancer, AIDS and cystic fibrosis.

As used herein, "catalytic nucleic acid molecule" means a DNA molecule (also known in the art as a "DNAzyme") or RNA molecule (also known in the art as a "ribozyme") which specifically recognizes and cleaves a distinct target nucleic acid sequence. For both DNAzymes and ribozymes, the target nucleic acid sequence can be either DNA or RNA.

The nucleic acid sequence in which the known disorder-characterizing mutation(s) resides (i.e., the sequence amplified in the instant methods) can be a DNA or RNA sequence. These mutation(s) include, for example, point mutations, deletion mutations, insertion mutations and frame-shift mutations. Each of the amplified nucleic acid segment and catalytic nucleic acid molecule can be either DNA or RNA. In one embodiment, the amplified nucleic acid segment is RNA and the catalytic nucleic acid molecule is either DNA or RNA. In a further embodiment, the amplified nucleic acid segment is DNA and the catalytic nucleic acid molecule is either RNA or DNA (25).

Methods for isolating and amplifying nucleic acid molecules used in the instant invention are well known in the art. More specifically, methods of isolating a sample of nucleic acid molecules from the subject include, for example, phenol chloroform extraction, quick lysis, capture on columns and polymer capture (20, 26-29). Methods of amplifying a nucleic acid sequence include, for example, PCR, LCR, SDA and TMA (also known as (SSR)) (1-11).

Suitable conditions for contacting an amplified nucleic acid segment containing a target sequence with a catalytic nucleic acid molecule so as to permit specific recognition and cleavage of the target sequence are well known in the art. In addition, such conditions are exemplified in the Experimental Details section below.

Methods of determining whether a catalytic nucleic acid molecule cleaves an amplified nucleic acid segment are also routine in the art. Such methods include, by way of example, polyacrylamide gel electrophoresis and capillary electrophoresis (20, 30).

In the preferred embodiment of this invention, (a) the amplification is performed using a polymerase chain reaction; (b) the catalytic nucleic acid molecule is a 10-23 DNAzyme; and (c) the polymerase chain reaction employs a DNA primer (i.e., a "chimeric" primer) suitable for initiating amplification of the segment, which primer contains at least one purine ribonucleotide residue which serves as the 5' side of the site within the amplified segment recognized and cleaved by the 10-23 DNAzyme. This purine ribonucleotide residue in the chimeric primer is required for cleavage by the 10-23 DNAzyme. Thus, using this chimeric primer permits the 10-23 DNAzyme cleavage site to be generated in a PCR reaction. The chimeric primer can also include, for example, a ribonucleotide residue that serves as the 3' side of the site recognized and cleaved by the 10-23 DNAzyme.

In one form of this embodiment, the amplified segment is recognized and cleaved in trans by the DNAzyme. In another form, (a) the polymerase chain reaction employs a second DNA primer suitable for initiating amplification of the segment, which second primer comprises a zymogene encoding a 10-23 DNAzyme such that, upon amplification, the resulting amplified nucleic acid molecule comprises the 10-23 DNAzyme; and (b) the amplified nucleic acid segment is recognized and cleaved in cis by the DNAzyme.

As used herein, "cis" cleavage by a DNAzyme shall mean that the DNAzyme recognizes and cleaves a sequence coexisting therewith on the same amplified nucleic acid molecule. Trans cleavage shall mean that the DNAzyme cleaves a substrate located on a different molecule. Finally, "zymogene" shall mean a nucleic acid sequence which comprises the anti-sense (i.e. complementary) sequence of a catalytic nucleic acid molecule, and whose transcription product is the catalytic nucleic acid molecule itself.

This invention still further provides kits for use in practicing the instant diagnostic methods. The first instant kit comprises (a) a catalytic nucleic acid molecule which specifically recognizes and cleaves a target sequence present either (i) in a nucleic acid segment having a mutation known to be characteristic of a disorder or (ii) in the corresponding wild-type nucleic acid segment, but not both, and (b) a nucleic acid reagent suitable for use in amplifying the nucleic acid segment containing the target sequence.

In one embodiment, the kit comprises a plurality of catalytic nucleic acid molecules. The nucleic acid reagent suitable for use in amplifying the nucleic acid segment containing the target sequence can be, for example, a nucleic acid primer. In one embodiment, the kit comprises a plurality of such nucleic acid reagents.

More specifically, the second instant kit comprises (a) a 10-23 DNAzyme which specifically recognizes and cleaves a target sequence present either (i) in a nucleic acid segment having a mutation known to be characteristic of a disorder or (ii) in the corresponding wild-type nucleic acid segment, but not both, and (b) a DNA primer suitable for initiating amplification of the segment under polymerase chain reaction conditions, which primer contains at least one purine ribonucleotide residue which serves as the 5' side of the site within the amplified segment recognized and cleaved by the 10-23 DNAzyme.

The third instant kit comprises (a) a first DNA primer which comprises a zymogene encoding a 10-23 DNAzyme that specifically recognizes and cleaves a target sequence present either (i) in a nucleic acid segment having a mutation known to be characteristic of a disorder or (ii) in the corresponding wild-type nucleic acid segment, but not both, which first primer is suitable for initiating amplification of the segment under polymerase chain reaction conditions; and (b) a second DNA primer suitable for initiating amplification of the segment under polymerase chain reaction conditions, which second primer contains at least one purine ribonucleotide residue which serves as the 5' side of the site within the amplified segment recognized and cleaved by the 10-23 DNAzyme, such that, upon amplification, (i) the resulting amplified nucleic acid molecule comprises the 10-23 DNAzyme, and (ii) the amplified nucleic acid segment is recognized and cleaved in cis by the DNAzyme.

In one embodiment, the instant kits further comprise one or more of the following: (a) reagents useful for isolating a sample of nucleic acid molecules from a subject being diagnosed; (b) reagents useful for amplifying a nucleic acid segment present in the isolated sample, which segment is known to contain a mutation in a subject afflicted with the disorder; and (c) reagents useful for creating suitable reaction conditions for catalytic nucleic acid activity. The reagents in components (a)–(c) of the instant kits can either be obtained commercially or made according to well known methods in the art, as exemplified in the Experimental Details section below.

The components of the instant kits can be in solution or lyophilized as appropriate. In one embodiment, the components of the instant kits are in the same compartment, and in another embodiment, the components of the instant kit are in separate compartments. In the preferred embodiment, the kits further comprise instructions for use.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

The examples of DNAzymes and ribozymes listed below are based on a 10-23 DNAzyme (19) and are designed to cleave the following medically important targets. The examples of ribozymes listed below are based on the hammerhead ribozyme (12).

I. DNAzymes
  where
    R=purine, either A or G.
    Y=pyrimidine, either C, T or U.
    H=A, T, U, or C (not G).
    D=A, T, U, or G (not C).
    B=C, T, U, or G (not A).
    V=A, C, or G (not T, not U).
    W=T, U, or A.
    italics=bases which are artificially introduced by in vitro amplification using primers containing bases which are mismatched with respect to the target sequence.
    bold=target base or sequence for analysis.
    underlined=recognition site (RY/R).
    E=modified sequence (primer-induced artificial sequence).

```
A. Acquired Disease
(1) Cancer
(a) K-ras codon 12, position 2 - mutant (G to C, U or A)

5' - GUU GGA GCU GGU GGC GUA GGC - 3'      wildtype        SEQ ID NO:1
                                           RNA 5' - GUU GGA GCU GYU GGC GUA GGC - 3'      mutant RNA      SEQ ID NO:2

3' - CAA CCT CGA RA CCG CAT CCG - 5'       DNAzyme         SEQ ID NO:3
                 A  G
                G     G
               C       C
              A         T
              A         A
               C       G
                A     C
                   T 5' - GUU GGA GCU GAU GGC GUA GGC - 3'      mutant RNA      SEQ ID NO:4

3' - CAA CCU CGA CUA CCG CAU CCG - 5'      antisense

5' - GCC UAC GCC AUC AGC UCC AAC - 3'      antisense       SEQ ID NO:5

3' - CGG ATG CGG AG TCG AGG TTG - 5'       DNAzyme         SEQ ID NO:6
                 A  G
                G     G
               C       C
              A         T
              A         A
               C       G
                A     C
                   T
```

-continued (b) K-ras codon 13, position 1 - mutant (G to A, U or C)

```
5' - GGA GCU GGU GGC GUA GGC AAG - 3'      wildtype       SEQ ID NO:7
                                            RNA 5' - GGA GCU GGU HGC GUA GGC AAG - 3'      mutant RNA     SEQ ID NO:8

3' - CCT CGA C A DCG CAT CCG TTC - 5'      DNAzyme        SEQ ID NO:9
            A   G
           G     G
          C       C
         A         T
          A       A
           C     G
            A   C
              T
```

(c) H-ras codon 61, position 1 - mutant (C to G, U or A)

```
5' - ACC GCC GGC CAG GAG GAG - 3'          wildtype       SEQ ID NO:10
                                            RNA 5' - ACC GCC GGC DAG GAG GAG - 3'          mutant RNA     SEQ ID NO:11

3' - TGG CGG C G HTC CTC CTC - 5'          DNAzyme        SEQ ID NO:12
            A   G
           G     G
          C       C
         A         T
          A       A
           C     G
            A   C
              T
```

(d) H-ras codon 61, position 2 - mutant (A to C, G or U)

```
5' - ACC GCC GGC CAG GAG GAG - 3'          wildtype       SEQ ID NO:13
                                            RNA 3' - UGG CGG CCG GUC GUC CUC - 5'          E wildtype
                                            RNA 5' - CUC CUG CUG GCC GGC GGU - 3'          E wildtype     SEQ ID NO:14
                                            RNA 3' - GAG GA GAC CGG CCG CCA - 5'           DNAzyme        SEQ ID NO:15
            A   G
           G     G
          C       C
         A         T
          A       A
           C     G
            A   C
              T
```

(e) H-ras codon 61, position 3 - mutant (G to C or U)
(Note; G to A is a silent mutation)

```
5' - ACC GCC GGC CAG GAG GAG - 3'          wildtype       SEQ ID NO:16
                                            RNA 5' - ACC GCC GGC CAY GAG GAG - 3'          mutant RNA     SEQ ID NO:17

3' - UGG CGG CCG GUR CUC CUC - 5'          antisense

5' - CUC CUC RUG GCC GGC GGU - 3'          antisense      SEQ ID NO:18

3' - GAG GAG AC CGG CCG CCA - 5'           DNAzyme        SEQ ID NO:19
            A   G
           G     G
          C       C
         A         T
          A       A
           C     G
            A   C
              T
```

(f) N-ras codon 61, position 1 - mutant (C to A, G or U)

```
5' - GCU GGA CAA GAA GAG - 3'              wildtype RNA   SEQ ID NO:20
```

-continued

```
5' - GCU GGA DAA GAA GAG - 3'        mutant RNA      SEQ ID NO:21

3' - CGA CCU HUG CUU CUC - 5'        Æ mutant RNA    SEQ ID NO:22

5' - CUC UUC GUH UCC AGC - 3'        Æ mutant RNA    SEQ ID NO:23

3' - GAG AAG  AD AGG TCG - 5'        DNAzyme
             A   G
            G     G
            C     C
           A       T
           A       A
            C     G
             A   C
              T 5' - GCU GGA UAA GAA GAG - 3'        mutant RNA      SEQ ID NO:24

3' - CGA CC  ATT CTT CTC - 5'        DNAzyme         SEQ ID NO:25
            A   G
           G     G
           C     C
          A       T
          A       A
           C     G
            A   C
             T
```

(2) HIV 1 - AZT Resistance, Point Mutations (a) Codon 41 - mutant (A to U or C)

```
5' - UGU ACA GAA AUG GAA AAG - 3'    wildtype        SEQ ID NO:26
                                     RNA 5' - UGU ACA GAA YUG GAA AAG - 3'    mutant RNA      SEQ ID NO:27

3' - ACA TGT CT  RAC CTT TTC - 5'    DNAzyme         SEQ ID NO:28
            A   G
           G     G
           C     C
          A       T
          A       A
           C     G
            A   C
             T
```

(b) Codon 70 - mutant (A to G)

```
5' - GAC AGU ACU AAA UGG AGA AAA - 3'    wildtype    SEQ ID NO:29
                                         RNA 5' - GAC AGU ACU AGA UGG AGA AAA - 3'    mutant RNA  SEQ ID NO:30

3' - CTG TCA TGA TC  ACC TCT TTT - 5'    DNAzyme     SEQ ID NO:31
               A   G
              G     G
              C     C
             A       T
             A       A
              C     G
               A   C
                T
```

(c) Codon 215 - mutant (C to U or A)

```
5' - AGG UGG GGA UUU ACC ACA CCA GAC - 3' wildtype   SEQ ID NO:32
                                          RNA 5' - AGG UGG GGA UUU AUC ACA CCA GAC - 3' mutant RNA SEQ ID NO:33

3' - TCC ACC CCT AAA  AG TGT GGT CTG - 5' DNAzyme    SEQ ID NO:34
                    A   G
                   G     G
                   C     C
                  A       T
                  A       A
                   C     G
                    A   C
```

-continued

```
                    T
5' - AGG UGG GGA UUU AAC ACA CCA GAC - 3'  mutant RNA    SEQ ID NO:35

3' - TCC ACC CCT AAA T G TGT GGT CTG - 5'  DNAzyme       SEQ ID NO:36
                    A G
                   G   G
                   C   C
                  A     T
                   A   A
                    C G
                    A C
                     T
```

(d) Codon 74 - mutant (U to G confers ddT resistance)

```
5' - AAA UGG AGA AAA UUA GUA GAU - 3'      wildtype      SEQ ID NO:37
                                           RNA 5' - AAA UGG AGA AAA GUA GUA GAU - 3'      mutant RNA    SEQ ID NO:38

3' - TTT ACC TCT TTT AT CAT CTA - 5'       DNAzyme       SEQ ID NO:39
                   A G
                  G   G
                  C   C
                 A     T
                  A   A
                   C G
                   A C
                    T
```

B. Inherited Disease (1) Cystic Fibrosis (a) Codon 542 - wildtype

```
5' - UAGUUCUUGGAGAAGGU - 3'       wildtype RNA   SEQ ID NO:40

5' - UAGUUCGUGGAGAAGGU - 3'       E wildtype RNA SEQ ID NO:41

3' - ATCAAG ACCTCTTCCA - 5'       DNAzyme        SEQ ID NO:42
           A G
          G   G
          C   C
         A     T
          A   A
           C G
           A C
            T
```

Codon 542 - mutant (G to U)

```
5' - UAGUUCUUUGAGAAGGU - 3'       mutant RNA     SEQ ID NO:43

5' - UAGUUCGUUGAGAAGGU - 3'       E mutant RNA   SEQ ID NO:44

3' - ATCAAG AACTCTTCCA - 5'       DNAzyme        SEQ ID NO:45
           A G
          G   G
          C   C
         A     T
          A   A
           C G
           A C
            T
```

(b) Codon 551 - wildtype

```
5' - GAGUGGAGGUCAACGAG - 3'       wildtype RNA   SEQ ID NO:46

3' - CUCACCUCCAGUUGCUC - 5'       antisense

5' - CUCGUUGACCUCCACUC - 3'       antisense      SEQ ID NO:47

3' - GAGCAAC GGAGGTGAG - 5'       DNAzyme        SEQ ID NO:48
            A G
           G   G
           C   C
          A     T
```

```
               A     A
             C         G
              A     C
                 T
```

Codon 551 - mutant (G to A)

5' - GAGUGGAGAUCAACGAG - 3'          mutant RNA      SEQ ID NO:49

3' - CUCACCUCUAGUUGCUC - 5'          antisense

5' - CUCGUUGAUCUCCACUC - 3'          antisense       SEQ ID NO:50

```
3' - GAGCAAC AGAGGTGAG - 5'          DNAzyme         SEQ ID NO:51
            A     G
             G     G
            C       C
           A         T
            A     A
             C     G
              A     C
                 T
```

(c) Codon 508 - wildtype

5' - GAAAUAUCAUCUUGGUGUUU - 3'       wildtype RNA    SEQ ID NO:52

```
3' - CTTTATAG AGAAACCACAAA - 5'      DNAzyme         SEQ ID NO:53
            A     G
             G     G
            C       C
           A         T
            A     A
             C     G
              A     C
                 T
```

Codon 508 - mutant (CTT deletion)

5' - AAAUAUCAUUGGUGUUU - 5'          mutant RNA      SEQ ID NO:54

```
3' - TTTATAG AACCACAAA - 3'          DNAzyme         SEQ ID NO:55
            A     G
             G     G
            C       C
           A         T
            A     A
             C     G
              A     C
                 T
```

(2) a1-antitrypsin

Codon 342 - mutant (G to A)

5' - GACCAUCGACGAGAAAGG - 3'         wildtype RNA    SEQ ID NO:56

5' - GACCAUCGACAAGAAAGG - 3'         mutant RNA      SEQ ID NO:57

```
3' - CTGGTAGC GTTCTTTCC - 5'         DNAzyme         SEQ ID NO:58
            A     G
             G     G
            C       C
           A         T
            A     A
             C     G
              A     C
                 T
```

II. Ribozymes where bold = target base for analysis.
underlined = recognition site (UH).

A. Acquired Disease (1) Cancer

K-ras codon 12, position 1 - mutant (G to A, C or U)

```
5' - GUA GUU GGA GCU GGU GGC GUA - 3'      wildtype    SEQ ID NO:59
                                           RNA 5' - GUA GUU GGA GCU HGU GGC GUA - 3'      mutant RNA  SEQ ID NO:60

3' - CAU CAA CCU CGA  CA CCG CAU - 5'      Ribozyme    SEQ ID NO:61
               A    C
               A    U
               G  A   G
               C  G G A
               A  U U
               G  C
               G  C
               A    G
                G  U K-ras codon 12, position 2 - mutant (G to U)

5' - GUU GGA GCU GGU GGC GUA GGC- 3'       wildtype    SEQ ID NO:62
                                           RNA 5' - GUU GGA GCU GUU GGC GUA GGC- 3'       mutant RNA  SEQ ID NO:63

3' - CAA CCU CGA CA  CCG CAU CCG- 5'       Ribozyme    SEQ ID NO:64
              A    C
              A    U
              G  A   G
              C  G G A
              A  U U
              G  C
              G  C
              A    G
               G  U (2) HIV 1 - AZT resistance (a) Codon 41 - mutant (A to U or C)

5' - UGU ACA GAA AUG GAA AAG - 3'          wildtype    SEQ ID NO:26
                                           RNA 5' - UGU ACA GAA YUG GAA AAG - 3'          mutant RNA  SEQ ID NO:27

3' - ACA UGU CUU RAC CUU U

-continued (c) Codon 215 - mutant (C to U or A)

```
5' - AGG UGG GGA UUU ACC ACA CCA GAC - 3'    wildtype        SEQ ID NO:32
                                             RNA 5' - AGG UGG GGA UUU AWC ACA CCA GAC - 3'    mutant RNA      SEQ ID NO:69

3' - UCC ACC CCU AAA UWG UGU GGU CUG - 5'    antisense

5' - GUC UGG UGU GWU AAA UCC CCA CCU - 3'    antisense       SEQ ID NO:70

3' - CAG ACC ACA CWA  UU AGG GGU GGA - 5'    Ribozyme        SEQ ID NO:71
                  A  C
                  A   U
                  G A G
                  C G G A
                  A U U
                  G C
                  G C
                  A   G
                  G U
```

(d) Codon 74 - mutant (U to G confers ddT resistance)

```
5' - AAA UGG AGA AAA UUA GUA GAU - 3'     wildtype        SEQ ID NO:37
                                          RNA 5' - AAA UGG AGA AAA GUA GUA GAU - 3'     mutant RNA      SEQ ID NO:38

3' - UUU ACC UCU UUU CA  CAU CUA - 5'     Ribozyme        SEQ ID NO:72
                     A  C
                     A   U
                     G A G
                     C G G A
                     A U U
                     G C
                     G C
                     A   G
                     G U
```

B. Inherited Disease (1) Cystic Fibrosis (a) Codon 542 - wildtype

```
5' - UAGUUCUUGGAGAAGGUGGA - 3'            wildtype        SEQ ID NO:40
                                          RNA
3' - AUCAAGA CCUCUUCCACCU - 5'            Ribozyme        SEQ ID NO:73
          A  C
          A   U
          G A G
          C G G A
          A U U
          G C
          G C
          A   G
          G U
```

Codon 542 - mutant (G to U)

```
5' - UAGUUCUUUGAGAAGGU - 5'               mutant RNA      SEQ ID NO:43

3' - AUCAAGA ACUCUUCCA - 3'               Ribozyme        SEQ ID NO:74
          A  C
          A   U
          G A G
          C G G A
          A U U
          G C
          G C
          A   G
          G U
```

(b) Codon 551 - wildtype

```
5' - GAGUGGAGGUCAACGAG - 3'               wildtype        SEQ ID NO:46
RNA

3' - CUCACCUCCA UUGCUC - 5'               Ribozyme        SEQ ID NO:75
```

```
            A  C
            A  U
           G A  G
          C G  G A
           A U  U
            G  C
            G  C
            A   G
             G U
```

Codon 551 - mutant (G to A)

```
5' - GAGUGGAGAUCAACGAG - 3'          mutant RNA      SEQ ID NO:49

3' - CUCACCUCUA UUGCUC - 5'          Ribozyme        SEQ ID NO:76
            A  C
            A  U
           G A  G
          C G  G A
           A U  U
            G  C
            G  C
            A   G
             G U
```

(c) Codon 508 - wildtype

```
5' - GAAAUAUCAUCUUUGGUGUUU - 3'      wildtype        SEQ ID NO:52
                                     RNA 3' - CUUUAUAGUAGA ACCACAAA - 5'      Ribozyme        SEQ ID NO:77
            A  C
            A  U
           G A  G
          C G  G A
           A U  U
            G  C
            G  C
            A   G
             G U
              or
```

Codon 508 - mutant (CUU deletion)

```
5' - GAAAUAUCAUUGGUGUUU - 3'         mutant RNA      SEQ ID NO:52

3' - CUUUAUAGUA CCACAAA - 5'         Ribozyme        SEQ ID NO:78
            A  C
            A  U
           G A  G
          C G  G A
           A U  U
            G  C
            G  C
            A   G
             G U
```

(2) β-Globin

β+- black (poly A signal) - mutant (U to C)

```
5' - UCUGCCUAAUAAAAAACAU - 3'        wildtype        SEQ ID NO:79
                                     RNA 5' - UCUGCCUAACAAAAAACAU - 3'        mutant RNA      SEQ ID NO:80

3' - AGACGGAUUGUUUUUUGUA - 5'        antisense

5' - AUGUUUUUGUUAGGCAGA - 3'         antisense       SEQ ID NO:81

3' - UACAAAAAACA UCCGUCU - 5'        Ribozyme        SEQ ID NO:82
            A  C
            A  U
           G A  G
          C G  G A
           A U  U
            G  C
            G  C
            A   G
             G U
```

III. K-ras Analysis Using Ribozymes
A. Ribozymes Targeting Mutations at K-ras Codon 12

The sequence of the human K-ras gene at codon 12 is GGT. Point mutations are frequently observed in the first 2 bases in this sequence in association with cancer of the pancreas, lung and colon. Two ribozymes were designed to cleave mutant but not wild-type K-ras.

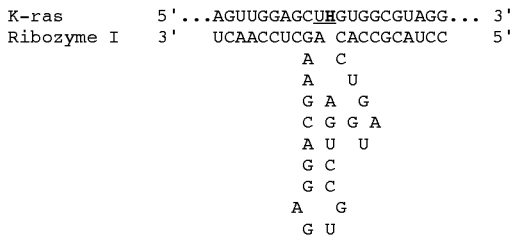

(K-ras codon 12-bold; Ribozyme target doublet—underlined)

Ribozyme I, above, is designed to cleave all RNA molecules which contain a point mutation at the first position of codon 12, but is designed not to cleave the wild-type sequence. The target sequence for the ribozyme is UH where H can equal C, U or A, but not G. Since the wild-type sequence is G at this position, all mutations will be cleaved with this ribozyme.

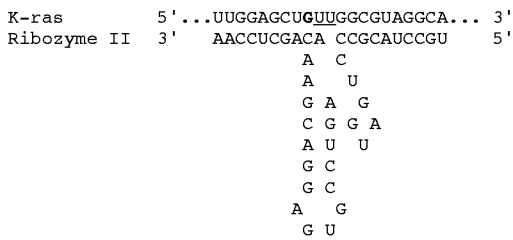

(K-ras codon 12 mutant allele—bold; Ribozyme target doublet—underlined)

Ribozyme II is designed to target G to U substitutions at position 2 of codon 12. The wild-type sequence G cannot base pair with the A at the first position within the hybridizing arms of the ribozyme, and hence the wild-type sequence is not expected to be cleaved with this ribozyme.

DNA sequences encoding ribozymes I and II were synthesized by Macromolecular Resources (Fort Collins, Colo.). The antisense and sense strands of the ribozymes were annealed and cloned into the vector pSP70 (Promega Corporation, Madison, Wis.) behind the T7 polymerase promoter. These clones were linearized at a site 3' to the ribozyme by digestion with Nde I, then purified. Radiolabelled ribozymes were prepared by standard in vitro RNA transcription reactions which incorporated [alpha-$^{32}$P] UTP using these templates (20).

B. Preparation of K-ras Templates

The human cell lines SW480 and Calu I were obtained from the American Type Culture Collection (Rockville, Md.). The colon carcinoma cell line SW480 has a homozygous mutation (GTT) at position 2 within codon 12 of K-ras. Calu 1 is a lung carcinoma cell line which is heterozygous at position 1 within K-ras codon 12 having both wild-type (GGT) and mutant (TGT) alleles.

K-ras DNA templates (4 mutant and 1 wild-type at codon 12) were generated by PCR amplification of Calu 1 and SW480 DNA, as well as pUC plasmid clones which contained K-ras inserts that were mutant at codon 12. The sequence of the 5' PCR primer was (SEQ ID NO:87) TGGACTTAATACGACTCACTATAGGGC-GACTGAATATAAACTTGTGGTAG. This 5' primer incorporated the T7 promoter at the 5' end. The sequence of the 3' primer was (SEQ ID NO:88) CCTCTATTGTTGGAT-CATATTCG. Radiolabelled K-ras RNA templates were generated by using the T7/K-ras PCR products in standard in vitro RNA transcription reactions which incorporated [alpha-$^{32}$P] UTP (20).

C. Detection of Point Mutations

In vitro cleavage experiments were performed as follows. Ribozyme and substrate were incubated in cleavage buffer (10 mM MgCl$_2$; 250 mM Tris.Cl, pH 7.5) in a 4:1 molar ratio. The ribozymes I and II were incubated with the radiolabelled K-ras RNA templates at 50° C. for 6 hr to assess in vitro cleavage ability. Reactions were analyzed by polyacryamide gel electrophoresis. Ribozyme I successfully cleaved K-ras RNA which contained a C, A or U mutation at codon 12 position 1 but was unable to cleave the wild-type sequence G. Ribozyme II successfully cleaved K-ras RNA which contained a U mutation at codon 12 position 2 but was unable to cleave the wild-type sequence G. The presence of cleaved K-ras RNA is therefore diagnostic for the presence of point mutations at codon 12.

This analysis demonstrates the ability of catalytic nucleic acids to specifically cleave templates in vitro which provides the basis for diagnose the presence of mutant sequences associated with disease. Nucleic acid can be amplified by a variety of techniques, e.g., PCR or TMA, and then cleaved with catalytic nucleic acids, e.g., DNAzyme (10-23 model) or ribozyme. The method can be used for detection of point mutations in K-ras which are specifically associated with cancer of the lung, colon and pancreas. The approach can be applied to diagnosis of any disease which is characterized by the presence of either an acquired or inherited genetic mutation.

IV. K-ras Mutation Analysis Using 10-23 DNAzymes and Chimeric Primers

Walder, et al. (38) have previously shown that Taq DNA polymerase can extend DNA/RNA chimeric primers that contain one or two 3' terminal ribose residues. Santoro and Joyce (19) showed cleavage of DNA/RNA chimeric substrates by the 10-23 DNAzyme. Chimeric primers are used here to produce PCR amplicons that serve as substrates for the 10-23 DNAzyme.

A. Use of DNAzymes for Distinguishing Variant Alleles; Targeting Sequences with DNAzymes Supplied In Trans Cleavage of a DNAzyme substrate produced from a chimeric primer can be achieved by adding a chemically synthesised DNAzyme to the PCR mix. In such a reaction, the DNAzyme cleaves the substrate in the trans orientation.

(1) DNAzymes Targeting Mutations at K-ras Codon 12; Natural Cleavage Site (a) Strategy PCR using a 5' DNA/RNA chimeric primer (5K42r) and a 3' primer (3K2) amplified a region of the K-ras gene. 5K42r hybridized to the K-ras sequence adjacent to codon 12 and contained the purine:pyrimidine residues which formed the potential DNAzyme cleavage site. The chimeric primer is fully complementary to the K-ras sequence that thus provided a natural cleavage site for a 10-23 DNAzyme. Extension from the 3' end of 5K42r by Taq DNA polymerase amplified codon 12 of the K-ras gene. A DNAzyme, Dz1, was designed to cleave amplicons that harbor wild-type sequence at codon 12 of K-ras. The 5' arm of the DNAzyme was fully complementary to sequences that are wild-type at codon 12. Mutations at K-ras codon 12, which result in mismatches with the 5' DNAzyme-hybridizing arm, were predicted to significantly decrease the efficiency of DNAzyme cleavage.

(b) Primer and DNAzyme Sequences

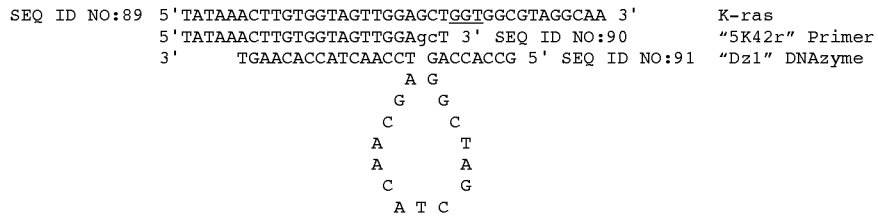

(Codon 12 in the K-ras wild-type sequence is underlined and the ribonucleotide bases in the primer 5K42r are in lower case letters.)

A further PCR primer, 3K2, was designed to produce an 82 base-pair amplicon when amplified with 5K42r. The sequence of 3K2 is:
5° CGTCCACAAAATGATTCTGA 3' SEQ ID NO:92 "3K2" Primer The primers and DNAzyme were synthesised by Pacific Oligos Pty. Ltd. (Lismore, NSW, Australia) or Oligos Etc., Inc. (Wilsonville, Oreg., USA). The DNAzyme Dz1 was modified by adding a 3' phosphate group to prevent extension by Taq DNA polymerase. The 5' primer, 5K42r, was 5' end-labelled with gamma-$^{32}$P by incubating 25 µl of 20 uM primer with 2.5 ul of Polynucleotide Kinase (10×10$^3$ U/ml, 3' phosphatase-free, Boehringer Mannheim), 2.5 µl RNasin (40 U/µl Recombinant RNasin®, Ribonuclease Inhibitor, Promega), 5 µl of polynucleotide kinase buffer (Boehringer Mannheim), 10 µl of gamma-$^{32}$P Adenosine 5'-Triphosphate (2.5 uM, Stable Label Gold™, Bresatec) and 5 µl of DEPC water for 30 minutes at 37° C.

(c) Preparation of K-ras Templates pUC 18 plasmid vectors containing K-ras exon 1 sequences, which were either wild-type (GGT) or mutated at codon 12 (CGT or AGT), were used as DNA templates for PCR.

(d) Detection of Point Mutations

PCR mixtures contained 0.2 pg/µl plasmid DNA, 10 pmole of gamma-$^{32}$P-labelled 5K42r, 2 pmole 3K2, 1 mM DTT, 8 mM MgCl$_2$, each dNTP (DATP, dCTP, dTTP, dGTP) at 100 uM, 0.4 U/µl RNasin®, and 1×buffer (100 mM NaCl with 50 mM Tris pH 8.3 at 25° C.). Duplicate reactions were set up with 0.5 uM Dz1, and single reactions without Dz1 were set up as control reactions. Six units of Taq DNA polymerase (5 U/µl AmpliTaq, Perkin-Elmer) were mixed with TaqStart™ antibody (Clontech) to give a final molar ratio of Taq DNA polymerase:TaqStart™ antibody of 1:5. The Taq DNA polymerase:TaqStart™ antibody mixture was incubated for 15 minutes at room temperature prior to addition to the PCR mix. The total reaction volumes were 50 µl. The reactions were placed in a GeneAmp PCR 9600 (Perkin-Elmer) and denatured at 94° C. for 2 minutes, then subjected to 15 cycles of 60° C. for 1 minute, followed by 94° C. for 20 seconds. The reaction was further subjected to 25 cycles of 40° C. for 1 minute followed by 94° C. for 20 seconds.

A 2.5 µl aliquot of each reaction was mixed with 2.5 µl of loading dye (97.5% formamide, 0.1% xylene cyanol, 0.1% bromophenol blue and 0.01 M EDTA), incubated at 75° C. for 2 minutes and then loaded immediately onto a prewarmed 16% denaturing (urea) acrylamide gel. The gels were electrophoresed for approximately one hour. The PCR product and cleavage fragments were visualised by scanning the gel using a Molecular Dynamics Phosphorimager 445 S1.

Several bands were visible on the gel (data not shown). The fragments, in order of mobility from the slowest to the fastest (i.e., from the origin to the bottom of the gel) were (a) PCR amplicons (running as a doublet), (b) unincorporated primer, and (c) cleaved PCR amplicons. Small amounts of two fragments, produced by background hydrolysis at the ribonucleotide residues within the 5'primer, were also visible running between the primer and cleaved amplicons and running parallel with the cleaved amplicons. In all reactions, PCR product and unincorporated primer were visible. Reactions containing template DNA that was wild-type at codon 12 (i.e., fully complementary to the DNAzyme) contained cleaved amplicons. Reactions containing template DNA that was mutated at codon 12 (i.e., mismatched with the DNAzyme) did not contain cleaved amplicons. Only low levels of background hydrolysis products were visible at this position on the gel in these reactions.

(2) DNAzymes Targeting Mutations at K-ras Codon 12; Induced Cleavage Site (a) Strategy PCR using a 5' DNA/RNA chimeric primer (5K44r) and a 3' primer (3K2) amplified a region of the K-ras gene. 5K44r hybridized to the K-ras sequence adjacent to codon 12 and contained the purine:pyrimidine residues which formed the potential DNAzyme cleavage site. The purine ribonucleotide in 5K44r was mismatched with respect to the K-ras template where the wild-type sequence has a pyrimidine at this position. This primer therefore induces a DNAzyme cleavage site. Extension from the 3' end of 5K44r by Taq DNA polymerase amplified codon 12 of the K-ras gene. A DNAzyme, Dz3, was designed to cleave amplicons that harbor wild-type sequence at codon 12 of K-ras. The 5' arm of the DNAzyme was fully complementary to sequences that are wild-type at codon 12. Mutations at K-ras codon 12, which result in mismatches with the 5' DNAzyme-hybridizing arm, were predicted to significantly decrease the efficiency of DNAzyme cleavage.
(b) Design of PCR Primers and DNAzymes

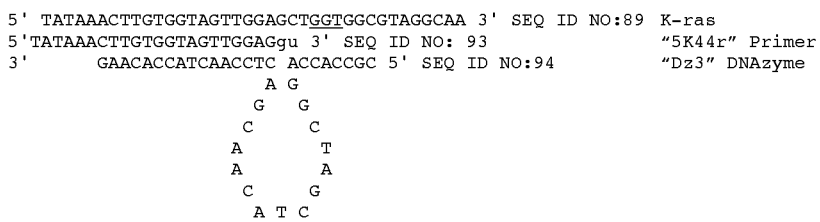

(Codon 12 in the K-ras wild-type sequence is underlined, and the ribonucleotide bases in the primer 5K44r are in lower case letters. The ribonucleotide "g" in the primer 5K44r is mismatched with respect to the K-ras sequence.)

A further PCR primer, 3K2, was designed to produce an 82 base-pair amplicon when amplified with 5K44r. The sequence of 3K2 is:
5' CGTCCACAAAATGATTCTGA 3' SEQ ID NO:92
"3K2" Primer The primers and DNAzyme were synthesised by Pacific Oligos Pty. Ltd. (Lismore, NSW, Australia) or Oligos Etc., Inc. (Wilsonville, Oreg., USA) The DNAzyme Dz3 was modified by adding a 3' phosphate group to prevent extension by Taq DNA polymerase. The 5' primer, 5K44r, was 5' end-labelled with gamma-$^{32}$P by incubating 25 µl of 20 uM primer with 2.5 µl of polynucleotide kinase ($10 \times 10^3$U/ml, 3' phosphatase-free, Boehringer Mannheim), 2.5 ul RNasin (40 U/µl Recombinant RNasin®, Ribonuclease Inhibitor, Promega), 5 µl of polynucleotide kinase buffer (Boehringer Mannheim), 10 µl of gamma-$^{32}$P Adenosine 5'-Triphosphate (2.5 µM, Stable Label Gold™, Bresatec) and 5 µl of DEPC water for 30 minutes at 37° C.
(c) Preparation of K-ras Templates pUC 18 plasmid vectors containing K-ras exon 1 sequences, which were either wild-type (GGT) or mutated at codon 12 (CGT), were used as DNA templates for PCR.
(d) Detection of Point Mutations PCR mixtures contained 0.2 pg/µl plasmid DNA, 10 pmole of gamma-$^{32}$P-labelled 5K44r, 2 pmole 3K2, 1 mM DTT, 8 mM MgCl$_2$, each dNTP (dATP, dCTP, dTTP, dGTP) at 100 µM, 0.4 U/µl RNasin®, and 1×buffer (100 mM NaCl with 50 mM Tris pH 8.3 at 25° C.). Duplicate reactions were set up with 0.5 µM Dz3 DNAzyme, and single reactions without Dz3 were set up as control reactions. Six units of Taq DNA polymerase (5 U/µl AmpliTaq, Perkin-Elmer) were mixed with TaqStart™ antibody (Clontech) to give a final molar ratio of Taq DNA polymerase:TaqStart™ antibody of 1:5. The Taq DNA polymerase:TaqStart™ antibody mixture was incubated for 15 minutes at room temperature prior to addition to the PCR mix. The total reaction volumes were 50 µl. The reactions were placed in a GeneAmp PCR 9600 (Perkin-Elmer) and denatured at 94° C. for 2 minutes, then subjected to 30 cycles of 60° C. for 1 minute, followed by 94° C. for 20 seconds. The reaction was further subjected to 10 cycles of 50° C. for 1 minute followed by 94° C. for 20 seconds.

A 2.5 µl aliquot of each reaction was mixed with 2.5 µl of loading dye (97.5% formamide, 0.1% xylene cyanol, 0.1% bromophenol blue and 0.01 M EDTA), incubated at 75° C. for 2 minutes and then loaded immediately onto a pre-warmed 16% denaturing (urea) acrylamide gel. The gels were electrophoresed for approximately 1 hour. The PCR product and cleavage fragments were visualised by scanning the gel using a Molecular Dynamics Phosphorimager 445 SI.

Several bands were visible on the gel (data not shown). The fragments, in order of mobility from the slowest to the fastest (i.e., from the origin to the bottom of the gel) were (a) PCR amplicons (running as a doublet), (b) unincorporated primer, and (c) cleaved PCR amplicons. Small amounts of a fragment, produced by background hydrolysis at the ribonucleotide bond within the 5'primer, was also visible running parallel with the cleaved amplicons. In all reactions, PCR product and unincorporated primer were visible. Reactions containing template DNA that was wild-type at codon 12 (i.e., fully complementary to the DNAzyme) contained cleaved amplicons. Reactions containing template DNA that was mutated at codon 12 (i.e., mismatched with the DNAzyme) did not contain cleaved amplicons. Only low levels of background hydrolysis products were visible at this position on the gel in these reactions.

B. DNAzymes Targeting Mutations at K-ras Codon 12; Cleavage in cis Orientation

Cleavage of amplicons produced from a chimeric primer can also be achieved using active DNAzymes that are synthesised during PCR. In one example of such a reaction the DNAzyme is cleaving the substrate in the cis orientation.
(a) Strategy PCR using a 5' DNA/RNA chimeric primer (5K42r) and a 3' zymogene primer (3K42Dz2) amplified a region of the K-ras gene. 5K42r hybridized to the K-ras sequence adjacent to codon 12 and contained the purine:pyrimidine residues which formed the potential DNAzyme cleavage site. The zymogene primer 3K42Dz2 had a 3' region that was complementary to K-ras, and a 5' region that contained the antisense of a DNAzyme. The zymogene primer had no inherent catalytic activity itself but, when used in conjunction with 5K42r, it facilitated the production of amplicons which had a DNAzyme cleavage site near their 5 termini and active (sense) DNAzymes at their 3'termini. The DNAzyme is designed to cleave the 5' end of the amplicons in cis. The 5' arm of the DNAzyme was fully complementary to sequences that are wild-type at codon 12. Mutations at K-ras codon 12, which result in mismatches with the 5' DNAzyme arm, were predicted to significantly decrease the efficiency of DNAzyme cleavage.
(b) Primer Sequences 5' chimeric primer 5K42r (upper case—deoxyribonucleotide residues; lower case—ribonucleotide residues)

SEQ ID NO:90 5' TATAAACTTGTGGTAGTTGGAgcT 3'

3' zymogene primer 3K42Dz2 (complement (antisense) of 10:23 catalytic core in bold)

SEQ ID NO:95 5' ACTTGTGGTAGTTGGATCGTTG-
TAGCTAGCCCTGGTGGCAGCTGTATCGT-
CAAGGCACTC 3'

The primers were synthesised by Pacific Oligos Pty. Ltd. (Lismore, NSW, Australia) or Oligos Etc., Inc. (Wilsonville, Oreg., USA). The 5' primer, 5K42r, was 5' end-labelled with gamma-$^{32}$P by incubating 25 μl of 20 μM primer with 2.5 μl of polynucleotide kinase (10×10$^3$ U/ml, 3' phosphatase-free, Boehringer Mannheim), 2.5 μl RNasin (40 U/μl Recombinant RNasin®, Ribonuclease Inhibitor, Promega), 5 μl of polynucleotide kinase buffer (Boehringer Mannheim), 10 μl of gamma-$^{32}$P Adenosine 5'-Triphosphate (2.5 μM, Stable Label Gold™, Bresatec) and 5 μl of DEPC water for 30 minutes at 37° C.

(c) K-ras DNA Templates pUC 18 plasmid vectors containing K-ras exon 1 sequences, which were either wild-type (GGT) or mutated at codon 12 (CGT or AGT), were used as DNA templates for PCR.

(d) Cleavage in cis by DNAzymes Synthesised During the PCR

PCR mixtures contained 0.2 pg/μl K-ras plasmid DNA, 10 pmole of gamma-$^{32}$P-labelled 5K42r, 2 pmole 3K42Dz2, 1 mM DTT, 8 mM MgCl$_2$, each dNTP (dATP, dCTP, dTTP, dGTP) at 100 uM, 0.4 U/μl RNasin®, and 1×buffer (100 mM NaCl with 50 mM Tris pH 8.3 at 25° C.). Duplicate reactions were set up for each DNA template. Six units of Taq DNA polymerase (5 U/μl AmpliTaq, Perkin-Elmer) were mixed with TaqStart™ antibody (Clontech) to give a final molar ratio of Taq DNA polymerase:TaqStart™ antibody of 1:5. The Taq DNA polymerase:TaqStart™ antibody mixture was incubated for 15 minutes at room temperature prior to addition to the PCR mix. The total reaction volumes were 50 μl. The reactions were placed in a GeneAmp PCR 9600 (Perkin-Elmer), denatured at 94° C. for 2 minutes, subjected to 30 cycles at 60° C. for 1 minute, followed by treatment at 94° C. for 20 seconds. The reaction was further subjected to 10 cycles at 50° C. for 1 minute, followed by treatment at 94° C. for 20 seconds.

A 2.5 μl aliquot of each reaction was mixed with 2.5 μl of loading dye (97.5% formamide, 0.1% xylene cyanol, 0.1% bromophenol blue and 0.01 M EDTA), incubated at 75° C. for 2 minutes, and then loaded immediately onto a pre-warmed 16% denaturing (urea) acrylamide gel. The gels were electrophoresed for approximately 1 hour. The PCR product and cleavage fragments were visualized by scanning the gel using a Molecular Dynamics Phosphorimager 445 S1.

Several bands were visible on the gel (data not shown). The fragments, in order of mobility from the slowest to the fastest (i.e., from the origin to the bottom of the gel) were (a) PCR amplicons (running as a doublet), (b) unincorporated primer, and (c) cleaved PCR amplicons. Small amounts of two fragments, produced by background hydrolysis at the ribonucleotide residues within the 5'primer, were also visible running between the primer and cleaved amplicons and running parallel with the cleaved amplicons. In all reactions, PCR product and unincorporated primer were visible. Reactions containing template DNA that was wild-type at codon 12 (i.e., fully complementary to the DNAzyme) contained cleaved amplicons. Reactions containing template DNA that was mutated at codon 12 (i.e., mismatched with the DNAzyme) did not contain cleaved amplicons. Only low levels of background hydrolysis products were visible at this position on the gel in these reactions.

The sequence below is an amplicon that is wild-type at position 1 of codon 12 (underlined) shown in a conformation wherein the DNAzyme (bold) is hybridizing in cis.

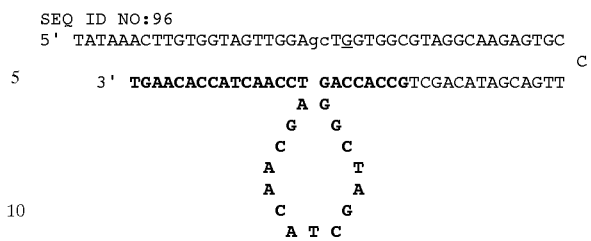

```
SEQ ID NO:96
5' TATAAACTTGTGGTAGTTGGAgcTGGTGGCGTAGGCAAGAGTGC
                                                        C
     3' TGAACACCATCAACCT GACCACCGTCGACATAGCAGTT
                          A G
                          G   G
                          C   C
                          A   T
                          A   A
                          C   G
                          A T C
```

V. CONCLUSION

The instant diagnostic methods are advantageous. Catalytic nucleic acids can require as few as two base pairs of specific sequence to create a cleavage site. Catalytic nucleic acid dinucleotide cleavage sites occur naturally at a greater frequency than do restriction enzyme cleavage sites. Furthermore, mismatched primers can be used to induce cleavage sites for catalytic nucleic acids in the same way that mismatched primers have been used to induce artificial restriction enzyme cleavage sites.

Examples of catalytic nucleic acids which require only a dinucleotide sequence at the cleavage site are the hammerhead ribozyme and the 10-23 DNAzyme. Both these molecules also require complementarity between the hybridizing regions (arms) and the molecule to be cleaved. However these regions can be made target-specific. Although catalytic nucleic acid molecules can only cleave single-stranded nucleic acid templates, methods of generating suitable single-stranded templates are well known in the art. For example, single-stranded RNA templates can be generated by a protocol such as TMA, and single-stranded DNA can be generated by asymmetric PCR (37) or by the denaturation of double-stranded products.

The instant methods provide a new tool for sequence analysis that is potentially more flexible than analysis by RFLP. The combination of nucleic acid amplification with catalytic nucleic acid cleavage overcomes the limitations of analysis using restriction enzymes. Here, the minimum sequence requirement for cleavage has been reduced. Furthermore, since the catalytic nucleic acid must also be complementary in the hybridizing region, these regions which flank the dinucleotide cleavage site will also effect cleavage efficiency. The length of sequence scanned by one catalytic nucleic acid can therefore be greater than that scanned by a single restriction enzyme. The analysis of sequences using catalytic nucleic acids also has an advantage over other protocols since here, no protein enzymes (e.g., restriction enzymes or RNAase A) or toxic compounds are required.

REFERENCES

1. Mullis, K. B., U.S. Pat. No. 4,683,202.
2. Arnheim, N., et al., U.S. Pat. No. 4,683,195.
3. Arnheim, N., et al., U.S. Pat. No. 4,000,159.
4. Ehrlich H. A., et al., U.S. Pat. No. 4,965,188.
5. Ehrlich H. A., et al., U.S. Pat. No. 5,176,995.
6. F. F. Chehab, et al. (1987) Nature 329:293–294.
7. R. K. Saiki, et al. (1985) Science 230:1350–1354.
8. Barany, F. (1991) Proc. Natl. Acad. Sci. 88:189–193.
9. Walker, G. T., et al. (1992) Nucleic Acids Res. 20:1691.
10. Jonas, V., et al. (1993) Journal of Clinical Microbiology 31:2410–2416.
11. Fahy, E., et al. (1991) PCR Methods Appl 1: 25–33.
12. Haseloff, J. and Gerlach, W. L. (1988) Nature 334:585–591.

13. Breaker, R. R. and Joyce, G. (1994) *Chemistry and Biology* 1:223–229.
14. Koizumi, M., et al. (1989) *Nucleic Acids Research* 17:7059–7069.
15. E. Otsuka and M. Koizumi, Japanese Patent No. 4,235,919.
16. Kashani-Sabet, M., et al. (1992) *Antisense Research and Development* 2:3–15.
17. Raillard, S. A. and Joyce, G. F. (1996) *Biochemistry* 35:11693–11701.
18. Carmi, N., et al. (1996) *Chemistry and Biology* 3:1039–1046.
19. Santoro, S. W. and Joyce, G. (1997) *PNAS* 94:4262–4266.
20. *Promega Protocols and Applications Guide.* Titus, D. E. (Ed), Promega Corporation (1991).
21. Watson, J. D., Tooze, J. and Kurtz, D. T. (1983) *Recombinant DNA: A short Course*. Scientific American Books, New York.
22. Antonarakis, S. E. (1989) *New England Journal of Medicine* 320:153–163.
23. Perriman, R. and Gerlach, W. L. (1992) *Gene* 113:157–163.
24. Nollau-Wagener, P. (1997) *Clinical Chemistry* 43: 1114–1128.
25. Carmi, N., et al. (1996) *Chemistry and Biology* 3:1039–1046.
26. Kramvis, A., et al. (1996) *Journal of Clinical Microbiology* 34: 2731–2733.
27. Yong, S. L., Thomas, R. J. S. and Phillips, W. A. (1995) *Nucleic Acids Research* 23:1640.
28. Sambrook, J., Fritsch, E. F. and Maniatis, T. (1989) *Molecular Cloning: A Laboratory Manual*, 2nd Ed., New York: Cold Spring Harbour Laboratory Press.
29. Backus, J. W., et al., U.S. Pat. No. 5,582,988.
30. Wei, L., Dai-Shu, H., Ju, Y. and Andrieu, J.-M. (1994) *Nature* 368; 269–271.
31. Bradley, S. M., et al., PCT International Publication No. WO 84/01389.
32. Cohen, J. B. and Levinson, A. D. (1988) *Nature* 334:119–124.
33. Kumar, R. and Barbacid, M. (1988) *Oncogene* 3:647–651.
34. Todd, A. V., et al. (1991) *Leukemia* 5:160.
35. Levi, S., et al. (1991) *Cancer Res.* 6:1079.
36. Kwok, S., et al. (1990) *Nucleic Acids Research* 18:999–1005.
37. Gyllensten, U. B. and Erlich, H. A. (1988) *PNAS* 95:7652–7656.
38. Walder, R. Y., et al. (1993) Nucleic Acid Research 21(18):4339–4343.

---

SEQUENCE LISTING

<160> NUMBER OF SEQ ID NOS: 96

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: K-ras codon
      12, position 2-mutant (G to C, U or A)

<400> SEQUENCE: 1
guuggagcug guggcguagg c                                                  21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence:mutant RNA

<400> SEQUENCE: 2
guuggagcug yuggcguagg c                                                  21

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:DNAzyme for
      K-ras codon 12

<400> SEQUENCE: 3
gcctacgcca rggctagcta caacgaagct ccaac                                   35

<210> SEQ ID NO 4
<211> LENGTH: 21
<212> TYPE: RNA
<213> ORGANISM: Artificial Sequence

```
<220> FEATURE:
<223> OTHER INFORMATION: Description of Artificial Sequence:antisense to
      mutant RNA for K-ras codon

<400> SEQUENCE: 4
gcccaugcca ucagcuccaa c                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence:antisense

<400> SEQUENCE: 5
gccuacgcca ucagcuccaa c                                              21

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:DNAzyme

<400> SEQUENCE: 6
gttggagctg aggctagcta caacgaggcg taggc                               35

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence:mutant RNA
      for K-ras codon 13

<400> SEQUENCE: 7
ggagcuggug gcguaggcaa g                                              21

<210> SEQ ID NO 8
<211> LENGTH: 18
<212> TYPE: RNA
<213> ORGANISM: Artificial Sequence
<220> FEATURE:
<223> OTHER INFORMATION: Description of Artificial Sequence: K-ras codon
      13, position 1 - mutant (G to A, U or C)

<400> SEQUENCE: 8
ggagcuhgcg uaggcaag                                                  18

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: DNAzyme for
      k-ras codon 13 mutant RNA

<400> SEQUENCE: 9
cttgcctacg cdaggctagc tacaacgaag ctcc                                34

<210> SEQ ID NO 10
<211> LENGTH: 18
<212> TYPE: RNA
<213> ORGANISM: Artificial Sequence
<220> FEATURE:
<223> OTHER INFORMATION: Description of Artificial Sequence:wildtype RNA
      for H-ras codon 61
```

```
<400> SEQUENCE: 10
accgccggcc aggaggag                                                    18

<210> SEQ ID NO 11
<211> LENGTH: 18
<212> TYPE: RNA
<213> ORGANISM: Artificial Sequence
<220> FEATURE:
<223> OTHER INFORMATION: Description of Artificial Sequence:mutant RNA
      for H-ras codon 61, position 1 - mutant (C to G, U or A)

<400> SEQUENCE: 11
accgccggcd aggaggag                                                    18

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: DNAzyme for
      H-ras codon 61, position 1-mutant

<400> SEQUENCE: 12
ctcctccthg ggctagctac aacgacggcg gt                                    32

<210> SEQ ID NO 13
<211> LENGTH: 18
<212> TYPE: RNA
<213> ORGANISM: Artificial Sequence
<220> FEATURE:
<223> OTHER INFORMATION: Description of Artificial Sequence:wildtype RNA
      for H-ras codon 61

<400> SEQUENCE: 13
accgccggcc aggaggag                                                    18

<210> SEQ ID NO 14
<211> LENGTH: 18
<212> TYPE: RNA
<213> ORGANISM: Artificial Sequence
<220> FEATURE:
<223> OTHER INFORMATION: Description of Artificial Sequence:mutant RNA
      at position 2 - mutant (A to C, G or u)

<400> SEQUENCE: 14
cuccugcugg ccggcggu                                                    18

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:DNAzyme for
      H-ras codon 61

<400> SEQUENCE: 15
accgccggcc agggctagct acaacgaagg ag                                    32

<210> SEQ ID NO 16
<211> LENGTH: 18
<212> TYPE: RNA
<213> ORGANISM: Artificial Sequence
<220> FEATURE:
<223> OTHER INFORMATION: Description of Artificial Sequence:wildtype RNA
      for H-ras codon 61, position 3
```

```
<400> SEQUENCE: 16
accgccggcc aggaggag                                              18

<210> SEQ ID NO 17
<211> LENGTH: 18
<212> TYPE: RNA
<213> ORGANISM: Artificial Sequence
<220> FEATURE:
<223> OTHER INFORMATION: Description of Artificial Sequence:mutant RNA
      for H-ras codon 61, position 3 - mutant (G to C or U)

<400> SEQUENCE: 17
accgccggcc aygaggag                                              18

<210> SEQ ID NO 18
<211> LENGTH: 18
<212> TYPE: RNA
<213> ORGANISM: Artificial Sequence
<220> FEATURE:
<223> OTHER INFORMATION: Description of Artificial Sequence:antisense of
      mutant RNA for H-ras codon 61, position 3

<400> SEQUENCE: 18
cuccucrugg ccggcggu                                              18

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:DNAzyme for
      H-ras codon 61, position 3

<400> SEQUENCE: 19
accgccggcc aggctagcta caacgagagg ag                              32

<210> SEQ ID NO 20
<211> LENGTH: 15
<212> TYPE: RNA
<213> ORGANISM: Artificial Sequence
<220> FEATURE:
<223> OTHER INFORMATION: Description of Artificial Sequence:N-ras codon
      61, position 1 wildtype RNA

<400> SEQUENCE: 20
gcuggacaag aagag                                                 15

<210> SEQ ID NO 21
<211> LENGTH: 15
<212> TYPE: RNA
<213> ORGANISM: Artificial Sequence
<220> FEATURE:
<223> OTHER INFORMATION: Description of Artificial Sequence:mutant RNa
      (Cto a, G or U)

<400> SEQUENCE: 21
gcuggadaag aagag                                                 15

<210> SEQ ID NO 22
<211> LENGTH: 15
<212> TYPE: RNA
<213> ORGANISM: Artificial Sequence
<220> FEATURE:
<223> OTHER INFORMATION: Description of Artificial Sequence:AE mutant
      RNA for N-ras codon 61

<400> SEQUENCE: 22
```
cucuucguhu ccagc                                                    15

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:DNAzyme for
      N-ras codon 61 position 1 - mutant (C to A, G or U)

<400> SEQUENCE: 23
gctggadagg ctagctacaa cgagaagag                                     29

<210> SEQ ID NO 24
<211> LENGTH: 15
<212> TYPE: RNA
<213> ORGANISM: Artificial Sequence
<220> FEATURE:
<223> OTHER INFORMATION: Description of Artificial Sequence:mutant RNA
      for N-ras codon 61, position 1

<400> SEQUENCE: 24
gcuggauaag aagag                                                    15

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:DNAzyme for
      N-ras codon 61, position 1

<400> SEQUENCE: 25
ctcttcttag gctagctaca acgaccagc                                     29

<210> SEQ ID NO 26
<211> LENGTH: 18
<212> TYPE: RNA
<213> ORGANISM: Artificial Sequence
<220> FEATURE:
<223> OTHER INFORMATION: Description of Artificial Sequence:wildtype RNA
      for Codon 41 of HIV 1 - AZT resistance point mutations

<400> SEQUENCE: 26
uguacagaaa uggaaaag                                                 18

<210> SEQ ID NO 27
<211> LENGTH: 18
<212> TYPE: RNA
<213> ORGANISM: Artificial Sequence
<220> FEATURE:
<223> OTHER INFORMATION: Description of Artificial Sequence:mutant RNA
      for codon 41 of HIV 1 AZT resistance mutant with  A to U or C.

<400> SEQUENCE: 27
uguacagaay uggaaaag                                                 18

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence:DNAzyme

<400> SEQUENCE: 28
cttttccarg gctagctaca acgatctgta ca                                 32

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence:wildtype RNA
      for codon 70 - mutant (A to G)

<400> SEQUENCE: 29
gacaguacua aauggagaaa a                                         21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence:mutant RNA
      for codon 70 of HIV 1 - AZT Resistance

<400> SEQUENCE: 30
gacaguacua gauggagaaa a                                         21

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence:DNAzyme for
      Codon 70 HIV-1 AZT resistant mutant

<400> SEQUENCE: 31
ttttctccag gctagctaca acgactagta ctgtc                          35

<210> SEQ ID NO 32
<211> LENGTH: 24
<212> TYPE: RNA
<213> ORGANISM: Artificial Sequence
<220> FEATURE:
<223> OTHER INFORMATION: Description of Artificial Sequence:wildtype RNA
      for codon 215 of HIV 1 AZT resistance point mutant

<400> SEQUENCE: 32 aggugggau uuaccacacc agac                                       24

<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence:mutant RNA
      for codon 215

<400> SEQUENCE: 33 aggugggau uuaucacacc agac                                       24

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence:DNAzyme for
      codon 215 - mutant (C to U or A)

<400> SEQUENCE: 34
gtctggtgtg aggctagcta caacgaaaat ccccacct                       38

<210> SEQ ID NO 35
<211> LENGTH: 24
<212> TYPE: RNA
<213> ORGANISM: Artificial Sequence
<220> FEATURE:
<223> OTHER INFORMATION: Description of Artificial Sequence:mutant RNA
      for codon 215, mutant

<400> SEQUENCE: 35
agguggggau uuaacacacc agac                                              24

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence:DNAzyme for
      codon 215 - mutant

<400> SEQUENCE: 36
gtctggtgtg ggctagctac aacgataaat ccccacct                               38

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence:wildtype RNA
      for codon 74 - mutant (U to G confers ddT resistance)

<400> SEQUENCE: 37
aaauggagaa aauuaguaga u                                                 21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence:mutant RNA
      for codon 74

<400> SEQUENCE: 38
aaauggagaa aaguaguaga u                                                 21

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence:DNAzyme for
      codon 74

<400> SEQUENCE: 39
atctactagg ctagctacaa cgattttctc cattt                                  35

<210> SEQ ID NO 40
<211> LENGTH: 17
<212> TYPE: RNA
<213> ORGANISM: Artificial Sequence
<220> FEATURE:
<223> OTHER INFORMATION: Description of Artificial Sequence:wildtype RNA
      for codon 542 - wildtype cystic fibrosis

<400> SEQUENCE: 40
uaguucuugg agaaggu                                                      17

```
<210> SEQ ID NO 41
<211> LENGTH: 17
<212> TYPE: RNA
<213> ORGANISM: Artificial Sequence
<220> FEATURE:
<223> OTHER INFORMATION: Description of Artificial Sequence:AE wildtype
      RNA for codon 542

<400> SEQUENCE: 41
uaguucgugg agaaggu                                                  17

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence:DNAzyme for
      codon 542 - Cystic Fibrosis

<400> SEQUENCE: 42
accttctcca ggctagctac aacgagaact a                                  31

<210> SEQ ID NO 43
<211> LENGTH: 17
<212> TYPE: RNA
<213> ORGANISM: Artificial Sequence
<220> FEATURE:
<223> OTHER INFORMATION: Description of Artificial Sequence:mutant RNA
      for Codon 542 - mutant (G to U)

<400> SEQUENCE: 43
uaguucuuug agaaggu                                                  17

<210> SEQ ID NO 44
<211> LENGTH: 17
<212> TYPE: RNA
<213> ORGANISM: Artificial Sequence
<220> FEATURE:
<223> OTHER INFORMATION: Description of Artificial Sequence:mutant RNA
      codon 542 - mutant (G to U)

<400> SEQUENCE: 44
uaguucguug agaaggu                                                  17

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence:DNAzyme for
      cystic Fibrosis Codon 542 - mutant (G to U)

<400> SEQUENCE: 45
accttctcaa ggctagctac aacgagaact a                                  31

<210> SEQ ID NO 46
<211> LENGTH: 17
<212> TYPE: RNA
<213> ORGANISM: Artificial Sequence
<220> FEATURE:
<223> OTHER INFORMATION: Description of Artificial Sequence:wildtype RNA
      for Cystic fibrosis codon 551

<400> SEQUENCE: 46
gaguggaggu caacgag                                                  17

<210> SEQ ID NO 47
```

```
<211> LENGTH: 17
<212> TYPE: RNA
<213> ORGANISM: Artificial Sequence
<220> FEATURE:
<223> OTHER INFORMATION: Description of Artificial Sequence:cystic
      fibrosis codon 551 antisense

<400> SEQUENCE: 47
cucguugacc uccacuc                                                  17

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence:DNAzyme for
      Codon 551 -  wildtype

<400> SEQUENCE: 48
gagtggaggg gctagctaca acgacaacga g                                  31

<210> SEQ ID NO 49
<211> LENGTH: 17
<212> TYPE: RNA
<213> ORGANISM: Artificial Sequence
<220> FEATURE:
<223> OTHER INFORMATION: Description of Artificial Sequence:mutant RNA
      for Codon 551 - mutant (G to A)

<400> SEQUENCE: 49
gaguggagau caacgag                                                  17

<210> SEQ ID NO 50
<211> LENGTH: 17
<212> TYPE: RNA
<213> ORGANISM: Artificial Sequence
<220> FEATURE:
<223> OTHER INFORMATION: Description of Artificial Sequence:antisense
      for codon 551 - mutant (G to A)

<400> SEQUENCE: 50
cucguugauc uccacuc                                                  17

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence:DNAzyme for
      Codon 51 - mutant (G to A)

<400> SEQUENCE: 51
gagtggagag gctagctaca acgacaacga g                                  31

<210> SEQ ID NO 52
<211> LENGTH: 22
<212> TYPE: RNA
<213> ORGANISM: Artificial Sequence
<220> FEATURE:
<223> OTHER INFORMATION: Description of Artificial Sequence:wildtype RNA
      for Codon 508 - wildtype

<400> SEQUENCE: 52
gaaauaucau cuuugguugu uu                                            22

<210> SEQ ID NO 53
<211> LENGTH: 34
```

```
<212> TYPE: DNA
<213> ORGANISM: Artificial Sequence
<220> FEATURE:
<223> OTHER INFORMATION: Description of Artificial Sequence:DNAzyme for
      codon 08 - wildtype

<400> SEQUENCE: 53
aaacacaaag aggctagcta caacgagata tttc                                34

<210> SEQ ID NO 54
<211> LENGTH: 17
<212> TYPE: RNA
<213> ORGANISM: Artificial Sequence
<220> FEATURE:
<223> OTHER INFORMATION: Description of Artificial Sequence:mutant RNA
      for codon 508 - mutant (CTT deletion)

<400> SEQUENCE: 54
aaauaucauu gguguuu                                                   17

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence:DNAzyme for
      codon 508 - mutant (CTT deletion) for Cystic fibrosis

<400> SEQUENCE: 55
aaacaccagg ctagctacaa cgagatattt                                     30

<210> SEQ ID NO 56
<211> LENGTH: 18
<212> TYPE: RNA
<213> ORGANISM: Artificial Sequence
<220> FEATURE:
<223> OTHER INFORMATION: Description of Artificial Sequence:wildtype RNA
      for a1-antitrypsin codon 342 - mutant (G to A)

<400> SEQUENCE: 56
gaccaucgac gagaaagg                                                  18

<210> SEQ ID NO 57
<211> LENGTH: 18
<212> TYPE: RNA
<213> ORGANISM: Artificial Sequence
<220> FEATURE:
<223> OTHER INFORMATION: Description of Artificial Sequence:mutant RNA
      for
      codon 342 a1 antitrypsin

<400> SEQUENCE: 57
gaccaucgac aagaaagg                                                  18

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence:DNAzyme for
      codon 342 - mutant (G to A)

<400> SEQUENCE: 58
cctttcttgg gctagctaca acgacgatgg tc                                  32

<210> SEQ ID NO 59
<211> LENGTH: 21
```

```
<212> TYPE: RNA
<213> ORGANISM: Artificial Sequence
<220> FEATURE:
<223> OTHER INFORMATION: Description of Artificial Sequence:K-ras codon
      12, position 1 wildtype RNA

<400> SEQUENCE: 59
guaguuggag cugguggcgu a                                                21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence:mutant RNA
      for K-ras codon 12, position 1 - mutant (G to A, C or U)

<400> SEQUENCE: 60
guaguuggag cuhguggcgu a                                                21

<210> SEQ ID NO 61
<211> LENGTH: 42
<212> TYPE: RNA
<213> ORGANISM: Artificial Sequence
<220> FEATURE:
<223> OTHER INFORMATION: Description of Artificial Sequence:Ribozyme for
      K-ras codon 12, position 1

<400> SEQUENCE: 61
uacgccaccu gaugaguccg ugaggacgaa agcuccaacu ac                         42

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence:wildtype RNA
      K-ras codon 12, position 2 - mutant (G to U)

<400> SEQUENCE: 62
guuggagcug guggcguagg c                                                21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence:mutant RNA
      for K-ras codon 12, position 2 - mutant (G to U)

<400> SEQUENCE: 63
guuggagcug uuggcguagg c                                                21

<210> SEQ ID NO 64
<211> LENGTH: 42
<212> TYPE: RNA
<213> ORGANISM: Artificial Sequence
<220> FEATURE:
<223> OTHER INFORMATION: Description of Artificial Sequence:ribozyme for
      K-ras codon 12, position 2 - mutant (G to U)

<400> SEQUENCE: 64
gccuacgccc ugaugagucc gugaggacga aacagcucca ac                         42

<210> SEQ ID NO 65
<211> LENGTH: 18
<212> TYPE: RNA
```

<210> SEQ ID NO 65
<211> LENGTH: 18 (implied)
<213> ORGANISM: Artificial Sequence
<220> FEATURE:
<223> OTHER INFORMATION: Description of Artificial Sequence:antisense
    for HIV 1 AZT reistance Codon 41 mutant (A to U or C)

<400> SEQUENCE: 65
cuuuuccaru ucuguaca                                                18

<210> SEQ ID NO 66
<211> LENGTH: 39
<212> TYPE: RNA
<213> ORGANISM: Artificial Sequence
<220> FEATURE:
<223> OTHER INFORMATION: Description of Artificial Sequence:Ribozyme for HIV 1 AZt resistance codon 414 - mutant (A to U or C)

<400> SEQUENCE: 66
uguacagcug augaguccgu gaggacgaaa yuggaaaag 39

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence:antisense for HIV -1 AZT resistance codon 70 - mutant (A to G)

<400> SEQUENCE: 67
uuuucuccau cuaguacugu c 21

<210> SEQ ID NO 68
<211> LENGTH: 42
<212> TYPE: RNA
<213> ORGANISM: Artificial Sequence
<220> FEATURE:
<223> OTHER INFORMATION: Description of Artificial Sequence:hiv-1 AZT resistance codon 70 mutant (A to G) ribozyme

<400> SEQUENCE: 68
gacaguaccu gaugaguccg ugaggacgaa agauggagaa aa 42

<210> SEQ ID NO 69
<211> LENGTH: 24
<212> TYPE: RNA
<213> ORGANISM: Artificial Sequence
<220> FEATURE:
<223> OTHER INFORMATION: Description of Artificial Sequence:HIV - AZT resistance Codon 215 - mutant (C to U or A)

<400> SEQUENCE: 69
agguggggau uuawcacacc agac 24

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence:antisense of codon 215 - mutant

<400> SEQUENCE: 70
gucugguguu gwuaaauccc caccu 25

<210> SEQ ID NO 71
<211> LENGTH: 45
<212> TYPE: RNA
<213> ORGANISM: Artificial Sequence

```
<220> FEATURE:
<223> OTHER INFORMATION: Description of Artificial Sequence:ribozyme for
      codon 215 - mutant (C to U or A)

<400> SEQUENCE: 71
agguggggau ucugaugagu ccgugaggac gaaawcacac cagac                    45

<210> SEQ ID NO 72
<211> LENGTH: 42
<212> TYPE: RNA
<213> ORGANISM: Artificial Sequence
<220> FEATURE:
<223> OTHER INFORMATION: Description of Artificial Sequence:Ribozyme for
      HIV-1 codon 74 mutant (U to G confers ddT resistance)

<400> SEQUENCE: 72
aucuaccuga ugaguccgug aggacgaaac uuuucuccau uu                       42

<210> SEQ ID NO 73
<211> LENGTH: 41
<212> TYPE: RNA
<213> ORGANISM: Artificial Sequence
<220> FEATURE:
<223> OTHER INFORMATION: Description of Artificial Sequence:Ribozyme for
      codon 542 - wildtype Cystic Fibrosis

<400> SEQUENCE: 73
uccaccuucu cccugaugag uccgugagga cgaaagaacu a                        41

<210> SEQ ID NO 74
<211> LENGTH: 38
<212> TYPE: RNA
<213> ORGANISM: Artificial Sequence
<220> FEATURE:
<223> OTHER INFORMATION: Description of Artificial Sequence:Ribozyme for
      codon 542 - mutant (G to U)

<400> SEQUENCE: 74
accuucucac ugaugagucc gugaggacga aagaacua                            38

<210> SEQ ID NO 75
<211> LENGTH: 38
<212> TYPE: RNA
<213> ORGANISM: Artificial Sequence
<220> FEATURE:
<223> OTHER INFORMATION: Description of Artificial Sequence:Ribozyme for
      Codon 551 - wildtype Cystic Fibrosis

<400> SEQUENCE: 75
cucguucuga ugaguccgug aggacgaaac cuccacuc                            38

<210> SEQ ID NO 76
<211> LENGTH: 38
<212> TYPE: RNA
<213> ORGANISM: Artificial Sequence
<220> FEATURE:
<223> OTHER INFORMATION: Description of Artificial Sequence:Ribozyme for
      Codon 551 - mutant (G to A) of Cystic Fibrosis

<400> SEQUENCE: 76
cucguucuga ugaguccgug aggacgaaau cuccacuc                            38

<210> SEQ ID NO 77
<211> LENGTH: 42
<212> TYPE: RNA
<213> ORGANISM: Artificial Sequence
<220> FEATURE:
```

```
<223> OTHER INFORMATION: Description of Artificial Sequence:Ribozyme for
      Codon 508 - wildtype Cystic Fibrosis

<400> SEQUENCE: 77
aaacaccacu gaugaguccg ugaggacgaa agaugauauu uc                    42

<210> SEQ ID NO 78
<211> LENGTH: 39
<212> TYPE: RNA
<213> ORGANISM: Artificial Sequence
<220> FEATURE:
<223> OTHER INFORMATION: Description of Artificial Sequence:Ribozyme for
      cystic Fibrosis Codon 508 - mutant (CUU deletion)

<400> SEQUENCE: 78
aaacacccug augaguccgu gaggacgaaa ugauauuuc                        39

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence:beta-globin
      B+ - black (poly A signal) wildtype RNA

<400> SEQUENCE: 79
ucugccuaau aaaaaacau                                              19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence:beta-globin
      utant (U to C) RNA

<400> SEQUENCE: 80
ucugccuaac aaaaaacau                                              19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence:antisense
      for beta-globin mutant (U to C)

<400> SEQUENCE: 81 auguuuuug uuaggcaga                                               19

<210> SEQ ID NO 82
<211> LENGTH: 40
<212> TYPE: RNA
<213> ORGANISM: Artificial Sequence
<220> FEATURE:
<223> OTHER INFORMATION: Description of Artificial Sequence:Ribozyme for
      beta-globin poly A signal - mutant

<400> SEQUENCE: 82
ucugccucug augaguccgu gaggacgaaa caaaaaacau                       40

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence:K-ras codon
```

12 target

<400> SEQUENCE: 83
aguuggagcu hguggcguag g                                              21

<210> SEQ ID NO 84
<211> LENGTH: 42
<212> TYPE: RNA
<213> ORGANISM: Artificial Sequence
<220> FEATURE:
<223> OTHER INFORMATION: Description of Artificial Sequence:Ribozyme I
      recognizing K-ras codon 12

<400> SEQUENCE: 84
ccuacgccac cugaugaguc cgugaggacg aaagcuccaa cu                       42

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence:K-ras target
      codon 12 mutant allele

<400> SEQUENCE: 85
uuggagcugu uggcguaggc a                                              21

<210> SEQ ID NO 86
<211> LENGTH: 42
<212> TYPE: RNA
<213> ORGANISM: Artificial Sequence
<220> FEATURE:
<223> OTHER INFORMATION: Description of Artificial Sequence:Ribozyme II
      for K-ras codon 12 mutant allele

<400> SEQUENCE: 86
ugccuacgcc cugaugaguc cgugaggacg aaacagcucc aa                       42

<210> SEQ ID NO 87
<211> LENGTH: 50
<212> TYPE: DNA
<213> ORGANISM: Artificial Sequence
<220> FEATURE:
<223> OTHER INFORMATION: Description of Artificial Sequence:K-ras primer

<400> SEQUENCE: 87
tggacttaat acgactcact atagggcgac tgaatataaa cttgtggtag               50

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 88
cctctattgt tggatcatat tcg                                            23

<210> SEQ ID NO 89
<211> LENGTH: 38
<212> TYPE: DNA
<213> ORGANISM: Artificial Sequence
<220> FEATURE:
<223> OTHER INFORMATION: Description of Artificial Sequence:K-ras wild
      type sequence fragment

<400> SEQUENCE: 89

```
tataaacttg tggtagttgg agctggtggc gtaggcaa                    38

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence:5K42r primer

<400> SEQUENCE: 90
tataaacttg tggtagttgg agct                                   24

<210> SEQ ID NO 91
<211> LENGTH: 39
<212> TYPE: DNA
<213> ORGANISM: Artificial Sequence
<220> FEATURE:
<223> OTHER INFORMATION: Description of Artificial Sequence:Dz1 DNAzyme

<400> SEQUENCE: 91
gccaccaggg ctagctacaa cgatccaact accacaagt                   39

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:3K2 primer

<400> SEQUENCE: 92
cgtccacaaa atgattctga                                        20

<210> SEQ ID NO 93
<211> LENGTH: 24
<212> TYPE: DNA
<213> ORGANISM: Artificial Sequence
<220> FEATURE:
<223> OTHER INFORMATION: Description of Combined DNA/RNA Molecule:primer
      5K44r primer
<223> OTHER INFORMATION: Description of Artificial Sequence:5K44r primer

<400> SEQUENCE: 93
tataaacttg tggtagttgg aggu                                   24

<210> SEQ ID NO 94
<211> LENGTH: 39
<212> TYPE: DNA
<213> ORGANISM: Artificial Sequence
<220> FEATURE:
<223> OTHER INFORMATION: Description of Artificial Sequence:Dz3 DNAzyme

<400> SEQUENCE: 94
cgccaccagg ctagctacaa cgactccaac taccacaag                   39

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence:3" zymogene
      primer eK42Dz2

<400> SEQUENCE: 95
acttgtggta gttggatcgt tgtagctagc cctggtggca gctgtatcgt caaggcactc    60
```

-continued

```
<210> SEQ ID NO 96
<211> LENGTH: 98
<212> TYPE: DNA
<213> ORGANISM: Artificial Sequence
<220> FEATURE:
<223> OTHER INFORMATION: Description of Artificial Sequence:codon  12
      position 1 wildtype amplicon

<400> SEQUENCE: 96
tataaacttg tggtagttgg agctggtggc gtaggcaaga gtgccttgac gatacagctg        60
ccaccagggc tagctacaac gatccaacta ccacaagt                                98
```

What is claimed is:

1. A method of determining whether a subject is afflicted with a disorder characterized by the presence of a known nucleic acid mutation, which comprises the steps of
   (a) isolating a sample of nucleic acid molecules from the subject;
   (b) (i) amplifying the nucleic acid segment present in the isolated sample, which segment is known to contain the mutation in a subject afflicted with the disorder, and (ii) under suitable conditions, contacting the resulting amplified segment with a catalytic nucleic acid molecule which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and
   (c) determining whether the catalytic nucleic acid molecule in step (b) (ii) cleaves the amplified segment, so as to determine whether the subject is afflicted with the disorder,
wherein the amplifying step and the step of contacting the amplified nucleic acid segment with catalytic nucleic acid molecule occurs in the same reaction vessel.

2. A method of determining whether a subject is afflicted with a disorder characterized by the presence of a plurality of known nucleic acid mutations, which comprises the steps of
   (a) isolating a sample of nucleic acid molecules from the subject;
   (b) (i) amplifying the nucleic acid segment present in the isolated sample, which segment is known to contain the plurality of mutations in a subject afflicted with the disorder, and (ii) under suitable conditions, contacting the resulting amplified segment with a plurality of catalytic nucleic acid molecules, each of which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and
   (c) determining whether each of the catalytic nucleic acid molecule sin step (b)(ii) cleaves the amplified segment, so as to determine whether the subject is afflicted with the disorder,
wherein the amplifying step and the step of contacting the amplified nucleic acid segment with catalytic nucleic acid molecule occurs in the same reaction vessel.

3. A method of determining whether a subject is afflicted with a disorder characterized by the presence of a plurality of known nucleic acid mutations, which comprises the steps of
   (a) isolating a sample of nucleic acid molecules from the subject;
   (b) (i) amplifying the nucleic acid segments present in the isolated sample, which segments collectively are known to contain the plurality of mutations in a subject afflicted with the disorder, and (ii) under suitable conditions, contacting the resulting amplified segments with a plurality of catalytic nucleic acid molecules, each of which specifically recognizes and cleaves a target sequence present either (1) in one of the nucleic acid segments having one of the known mutations or (2) in the corresponding wild-type nucleic acid segment, but not both, with the proviso that step (ii) can be performed either subsequent to or concurrently with step (i); and
   (c) determining whether each of the catalytic nucleic acid molecules in step (b)(ii) cleaves the amplified segment containing its respective target sequence, so as to determine whether the subject is afflicted with the disorder,
wherein the amplifying step and the step of contacting the amplified nucleic acid segment with catalytic nucleic acid molecule occurs in the same reaction vessel.

4. The method of claim 1, 2 or 3, wherein the subject is a human.

5. The method of claim 1, 2 or 3, wherein the disorder is selected from the group consisting of cancer, AIDS and cystic fibrosis.

6. The method of claim 5, wherein the disorder is cancer.

7. The method of claim 1, 2 or 3, wherein the amplified nucleic acid segment is RNA and the catalytic nucleic acid molecule is selected from the group consisting of DNA and RNA.

8. The method of claim 1, 2 or 3, wherein the amplified nucleic acid segment is DNA and the catalytic nucleic acid molecule is RNA or DNA.

9. A method of determining whether a subject is afflicted with a disorder characterized by the presence of a known nucleic acid mutation, which comprises the steps of
   (a) isolating a sample of nucleic acid molecules from the subject;
   (b) (i) amplifying the nucleic acid segment present in the isolated sample using a polymerase chain reaction, which segment is known to contain the mutation in a subject afflicted with the disorder, and (ii) under suitable conditions, contacting the resulting amplified segment with a catalytic nucleic acid molecule, 10-23 DNAzyme, which specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and (c) determining whether the catalytic nucleic acid molecule in step (b)(ii) cleaves the amplified segment, so as to determine whether the subject is afflicted with the disorder, wherein the polymerase chain reaction employs a DNA primer suitable for initiating amplification of the segment, which primer contains at least one purine ribonucleotide residue which serves as the 5' side of the site within the amplified segment recognized and cleaved by the 10-23 DNAzyme.

10. A method of determining whether a subject is afflicted with a disorder characterized by the presence of a plurality of known nucleic acid mutations, which comprises the steps of (a) isolating a sample of nucleic acid molecules from the subject;

(b) (i) amplifying the nucleic acid segment present in the isolated sample using a polymerase chain reaction, which segment is known to contain the plurality of mutations in a subject afflicted with the disorder, and (ii) under suitable conditions, contacting the resulting amplified segment with a plurality of catalytic nucleic acid molecules wherein at least one of the catalytic nucleic acid molecules is a 10-23 DNAzyme, and wherein each of the catalytic nucleic acid molecules specifically recognizes and cleaves a target sequence present either (1) in the nucleic acid segment having the known mutation or (2) in the corresponding wild-type nucleic acid segment, but not both, with the proviso that step (ii) can be performed either subsequent to or concurrently with step (i); and (c) determining whether each of the catalytic nucleic acid molecules in step (b)(ii) cleaves the amplified segment, so as to determine whether the subject is afflicted with the disorder, wherein the polymerase chain reaction employs a DNA primer suitable for initiating amplification of the segment, which primer contains at least one purine ribonucleotide residue which serves as the 5' side of the site within the amplified segment recognized and cleaved by the 10-23 DNAzyme.

11. A method of determining whether a subject is afflicted with a disorder characterized by the presence of a plurality of known nucleic acid mutations, which comprises the steps of (a) isolating a sample of nucleic acid molecules from the subject;

(b) (i) amplifying the nucleic acid segments present in the isolated sample using a polymerase chain reaction, which segments collectively are known to contain the plurality of mutations in a subject afflicted with the disorder, and (ii) under suitable conditions, contacting the resulting amplified segments with a plurality of catalytic nucleic acid molecules wherein at least one of the catalytic nucleic acid molecules is a 10-23 DNAzyme, and wherein each of the catalytic nucleic acid molecules specifically recognizes and cleaves a target sequence present either (1) in one of the nucleic acid segments having one of the known mutations or (2) in the corresponding wild-type nucleic acid segment, but not both, with the proviso that step (ii) can be performed either subsequent to or concurrently with step (i); and (c) determining whether each of the catalytic nucleic acid molecules in step (b)(ii) cleaves the amplified segment containing its respective target sequence, so as to determine whether the subject is afflicted with the disorder, and wherein the polymerase chain reaction employs a DNA primer suitable for initiating amplification of the segment, which primer contains at least one purine ribonucleotide residue which serves as the 5' side of the site within the amplified segment recognized and cleaved by the 10-23 DNAzyme.

12. The method of claim 9, 10 or 11 wherein the amplified segment is recognized and cleaved in trans by the DNAzyme.

13. The method of claim 9, 10 or 11, wherein (a) the polymerase chain reaction employs a second DNA primer suitable for initiating amplification of the segment, which second primer comprises a zymogene encoding a 10-23 DNAzyme such that, upon amplification, the resulting amplified nucleic acid molecule comprises the 10-23 DNAzyme; and (b) the amplified nucleic acid segment is recognized and cleaved in cis by the DNAzyme.

14. A kit for use in practicing the method of claim 1, 2 or 3, which comprises (a) a catalytic nucleic acid molecule which specifically recognizes and cleaves a target sequence present either (i) in a nucleic acid segment having a mutation known to be characteristic of a disorder or (ii) in the corresponding wild-type nucleic acid segment, but not both, and (b) a nucleic acid reagent suitable for use in amplifying the nucleic acid segment containing the target sequence.

15. A kit for use in practicing the method of claim 9, 10 or 11 which comprises (a) a 10-23 DNAzyme which specifically recognizes and cleaves a target sequence present either (i) in a nucleic acid segment having a mutation known to be characteristic of a disorder or (ii) in the corresponding wild-type nucleic acid segment, but not both, and (b) a DNA primer suitable for initiating amplification of the segment under polymerase chain reaction conditions, which primer contains at least one purine ribonucleotide residue which serves as the 5' side of the site within the amplified segment recognized and cleaved by the 10-23 DNAzyme.

16. A kit for use in practicing the method of claim 13, which comprises (a) a first DNA primer which comprises a zymogene encoding a 10-23 DNAzyme that specifically recognizes and cleaves a target sequence present either (i) in a nucleic acid segment having a mutation known to be characteristic of a disorder or (ii) in the corresponding wild-type nucleic acid segment, but not both, which first primer is suitable for initiating amplification of the segment under polymerase chain reaction conditions; and (b) a second DNA primer suitable for initiating amplification of the segment under polymerase chain reaction conditions, which second primer contains at least one purine ribonucleotide residue which serves as the 5' side of the site within the amplified segment recognized and cleaved by the 10-23 DNAzyme, such that, upon amplification, (i) the resulting amplified nucleic acid molecule comprises the 10-23 DNAzyme, and (ii) the amplified nucleic acid segment is recognized and cleaved in cis by the DNAzyme.

* * * * *